United States Patent
Kylhammar et al.

(10) Patent No.: US 10,300,084 B2
(45) Date of Patent: May 28, 2019

(54) METHODS FOR TREATING PULMONARY HYPERTENSION

(71) Applicant: Chiesi Farmaceutici S.p.A., Parma (IT)

(72) Inventors: David Kylhammar, Lund (SE); Goran Radegran, Lund (SE)

(73) Assignee: Chiesi Farmaceutici S.p.A., Parma (IT)

(*) Notice: Subject to any disclaimer, the term of this patent is extended or adjusted under 35 U.S.C. 154(b) by 0 days.

(21) Appl. No.: 15/004,880

(22) Filed: Jan. 22, 2016

(65) Prior Publication Data

US 2016/0136196 A1   May 19, 2016

Related U.S. Application Data

(63) Continuation of application No. 13/963,771, filed on Aug. 9, 2013, now abandoned, which is a continuation of application No. PCT/US2012/024411, filed on Feb. 9, 2012.

(60) Provisional application No. 61/441,081, filed on Feb. 9, 2011.

(51) Int. Cl.
*A61K 31/7076* (2006.01)
*A61K 45/06* (2006.01)
*A61K 9/00* (2006.01)

(52) U.S. Cl.
CPC ........ *A61K 31/7076* (2013.01); *A61K 9/0019* (2013.01); *A61K 45/06* (2013.01)

(58) Field of Classification Search
CPC ... A61K 31/7076; A61K 45/06; A61K 9/0019
USPC ........................................................ 514/47
See application file for complete search history.

(56) References Cited

U.S. PATENT DOCUMENTS

| | | |
|---|---|---|
| 5,721,219 A | 2/1998 | Ingall et al. |
| 5,955,447 A | 9/1999 | Ingall et al. |
| 6,114,313 A | 9/2000 | Bland et al. |
| 6,130,208 A | 10/2000 | Broadhead |
| 2006/0270607 A1 | 11/2006 | Dixon et al. |
| 2009/0048173 A1* | 2/2009 | Eisert .................. A61K 31/519 514/6.9 |

FOREIGN PATENT DOCUMENTS

| | | |
|---|---|---|
| CN | 1119869 | 4/1996 |
| WO | 2009/121031 | 10/2009 |
| WO | 2009/140407 | 11/2009 |

OTHER PUBLICATIONS

Glossary of medical education terms, Institute of International Medical Education. http://www.iime.org/glossary.htm Accessed in Mar. 2013.*
Galie et al. Guidelines for the diagnosis and treatment of pulmonary hypertension. European Heart Journal (2009) 30, 2493-2537.*
Bhatt et al. Intravenous Platelet Blockade with Cangrelor during PCI. N. Eng IJ Med 2009;361:2330•41.*
Dumitrascu et al. Activation of Soluble Guanylate Cyclase Reverses Experimental Pulmonary Hypertension and Vascular Remodeling. Circulation 2006;113:286-295.*
Noe et al., Regulators of Platelet cAMP Levels: Clinical and Therapeutic Implications., Curr. Med. Chem., 2010, 17(26), 2897-2905.
Hill et al., Postoperative Pulmonary Hypertension: Etiology and Treatment of a Dangerous Complication, Respiratory Care, 2009, 54(7), 958-968.
Simonneau et al., Updated Clinical Classification of Pulmonary Hypertension, JACC, 2009, 54(1), S43-S54.
Humbert, Update in Pulmonary Hypertension 2008, Am. J. Respir. Crit. Care Med., 2009, 179, 650-656.
Von Kugelgen, Pharmacology of Mammalian P2X- and P2Y- receptors, Biotrend Rev., 2008, 9-2008(3), 1-12.
Wallentin, P2Y12 Inhibitors: Differences in Properties and Mechanisms of Action and Potential Consequences for Clinical Use, Eur. Heart J, 2009, 30, 1964-1977.
Van Giezen, Optimizing Platelet Inhibition, Eur. Heart J. Suppl, 2008, 10, D23-D29.
Oestreich, Elinogrel, a reversible P2Y12 receptor antagonist for the treatment of acute coronary syndrome and prevention of secondary thrombotic events, Curr. Opin. Investig. Drugs, 2010, 11(3), 340-348.
Harrington et al., Platelet Inhibition with Cangrelor in Patients Undergoing PCI, N. Engl. J. Med., 2009, 361, 2318-2329.
Subias et al., Current diagnostic and prognostic assessment of pulmonary Hypertension, Rev. Esp. Cardiol., 2010, 63(5), 583-596.
Serebruany et al., Dyspnoea after antiplatelet agents: the AZD6140 controversy., Intl. J. Clin. Pract., Mar. 2007; 61(3): 529-33.
Bagram et al., Novosti Meditsiny I Pharmacii Newspaper, Cadiology (241) 2008 (themed issue) [online] [found on Dec. 12, 2015].
Ueno et al., Update on the clinical development of cangrelor., Expert Rev. Cardiovasc. Ther., Aug. 2010 8(8): 1069-77.
Van Der Giet et al., The role of P2Y receptors in control of blood pressure., Drug News Perspect., Dec. 2002; 15(10): 640-646.
Husted & van Giezen, Ticagrelor: The First Reversibly Binding Oral P2Y12 Receptor Antagonist, Cardiovascular Therapeutics, 2009, 27, 259-274.
Nakonechnicov et al. Platelet aggregation in patients with primary pulmonary hypertension. Blood Coagulation & Fibrinolysis: Mar. 1996, vol. 7, issue 2, pp. 225-7.

* cited by examiner

*Primary Examiner* — Yin-Horng Shiao
(74) *Attorney, Agent, or Firm* — Maryellen Feehery Hank; Vorys, Sater, Seymour and Pease LLP

(57) ABSTRACT

The present invention relates to methods for treating or preventing pulmonary hypertension, reducing mortality in a subject experiencing pulmonary hypertension, or inhibiting ADP-mediated vasoconstriction of pulmonary arteries in a subject, comprising administering to the subject an effective amount of a pharmaceutical composition comprising a reversible $P2Y_{12}$ receptor antagonist. Also provided are related medicaments, pharmaceutical compositions, and methods for preparing the medicaments.

15 Claims, No Drawings

METHODS FOR TREATING PULMONARY HYPERTENSION

CROSS-REFERENCE TO RELATED APPLICATIONS

This application is a continuation of U.S. application Ser. No. 13/963,771, filed on Aug. 9, 2013, which is a continuation of International Application No. PCT/US2012/024411, filed on Feb. 9, 2012, which claims the benefit of U.S. Provisional Application No. 61/441,081, filed on Feb. 9, 2011, the contents of each of the above applications of which are incorporated by reference herein, in their entireties and for all purposes.

FIELD OF THE INVENTION

The invention relates generally to methods for treating or preventing pulmonary hypertension or other related symptoms in a subject in need thereof, related medicaments, pharmaceutical compositions, and methods for preparing the medicaments.

BACKGROUND OF THE INVENTION

Pulmonary hypertension (PH) is a disease characterized by high blood pressure in lung vasculature, including pulmonary arteries, pulmonary veins, and pulmonary capillaries. In general, PH is defined as a mean pulmonary arterial (PA) pressure ≥25 mm Hg at rest or ≥30 mm Hg with exercise. Hill et al., *Respiratory Care* 54(7):958-68 (2009). The main PH symptom is difficulty in breathing or shortness of breath, and other symptoms include fatigue, dizziness, fainting, peripheral edema (swelling in foot, legs or ankles), bluish lips and skin, chest pain, angina pectoris, light-headedness during exercise, non-productive cough, racing pulse and palpitations. PH can be a severe disease causing heart failure, which is one of the most common causes of death in people who have pulmonary hypertension Postoperative pulmonary hypertension may complicate many types of surgeries or procedures, and present a challenge associated with a high mortality.

PH may be grouped based on different manifestations of the disease sharing similarities in pathophysiologic mechanisms, clinical presentation, and therapeutic approaches. Simonneau et al., *JACC* 54(1):S44-54 (2009). Clinical classification of PH was first proposed in 1973, and a recent updated clinical classification was endorsed by the World Health Organization (WHO) in 2008. According to the updated PH clinical classification, there are five main groups of PH: pulmonary arterial hypertension (PAH), characterized by a PA wedge pressure ≤15 mm Hg; PH owing to a left heart disease (also known as pulmonary venous hypertension or congestive heart failure), characterized by a PA wedge pressure >15 mm Hg; PH owing to lung diseases and/or hypoxia; chronic thromboemboli PH; and PH with unclear or multifactorial etiologies. Simonneau et al., *JACC* 54(1):S44-54 (2009); Hill et al., *Respiratory Care* 54(7): 958-68 (2009). PAH is further classified into idiopathic PAH (IPAH), a sporadic disease in which there is neither a family history of PAH nor an identified risk factor; heritable PAH; PAH induced by drugs and toxins; PAH associated with connective tissue diseases, HIV infection, portal hypertension, congenital heart diseases, schistosomiasis, and chronic hemolytic anemia; and persistent PH of newborns. Simonneau et al., *JACC* 54(1):S44-54 (2009). Diagnosis of various types of PH requires a series of tests.

PH treatment depends greatly on the cause or classification of the PH. Where PH is caused by a known medicine or medical condition, it is known as a secondary PH, and its treatment is usually directed at the underlying disease. Treatment of pulmonary venous hypertension generally involves optimizing left ventricular function by administering diuretics, beta blockers, and ACE inhibitors, or repairing or replacing a mitral valve or aortic valve. PAH therapies include pulmonary vasodilators, digoxin, diuretics, anticoagulants, and oxygen therapy. Pulmonary vasodilators target different pathways, including prostacyclin pathway (e.g., prostacyclins, including intravenous epoprostenol, subcutaneous or intravenous treprostinil, and inhaled iloprost), nitric oxide pathway (e.g., phosphodiesterase-5 inhibitors, including sildenafil and tadalafil), and endotheline-1 pathway (e.g., endothelin receptor antagonists, including oral bosentan and oral ambrisentan). Humbert, M. *Am. J. Respir. Crit. Care Med.* 179:650-6 (2009); Hill et al., *Respiratory Care* 54(7): 958-68 (2009). However, the current treatments provide no cure for the devastating PAH. Humbert, M. *Am. J Respir. Crit. Care Med* 179:650-6 (2009).

$P2Y_{12}$ receptor is a G-protein-coupled membrane-bound receptor that is selectively activated by adenine nucleotides, and expressed in platelets, microglia and neuronal tissues. Von Kügelgen, I. Pharmacology of mammalian P2X- and P2Y-receptors, in *BIOTREND Reviews*, No. 3 (9-2008). $P2Y_{12}$ receptor antagonists found to inhibit platelet aggregation include indirect, irreversible inhibitors such as thienopyridine prodrugs (e.g., ticlopidine, clopidogrel, and prasugrel), and direct, reversible inhibitors such as cangrelor (AR-C699311MX), ticagrelor (AZD6140), AR-C67085, and elinogrel (PRT-060128). Wallentin, L., *Eur. Heart J.* 30: 1964-77 (2009); Van Giezen, J. J. J. *Eur. Heart J. Suppl.* 1 10 (Suppl. D):D23-D29 (2008); Oestreich, J. H., *Curr. Opin. Drugs* 11(3):340-8 (2010).

Cangrelor is a rapid-acting, reversible adenosine diphosphate (ADP) receptor antagonist. It reaches steady state concentrations in plasma within 30 min of start of infusion (bolus 30 μg/kg and infusion 4 μg/kg/min), and is rapidly cleared from plasma with a short half-life of 3-6 min. Wallentin, L., *Eur. Heart J.* 30: 1964-77 (2009); Harrington et al., *N. Engl. J. Med.* 361:2318-29 (2009); Bhatt et al., *N. Engl. J. Med.* 361:2330-41 (2009).

$P2Y_{12}$ receptor is also expressed in vascular smooth muscle cells. Preclinical studies suggest that reversible $P2Y_{12}$ inhibition may be associated with beneficial effects on $P2Y_{12}$-mediated vasoconstriction, which effects may permit reduction in thrombogenic vasospasm or reduce deficits in myocardial perfusion after thrombsis. Husted & van Giezen, *Cardiovascular Therapeutic* 27:259-74 (2009). In particular, treatment with cangrelor or ticagrelor in a dog thrombosis model resulted in decreased reocclusion and cyclic flow variation, and improved myocardial flow compared with placebo in animals receiving tissue-type plasminogen activator and heparin after thrombus formation, Husted & van Giezen, *Cardiovascular Therapeutic* 27:259-74 (2009). However, no therapeutic effects of $P2Y_{12}$ reversible antagonists have been reported on pulmonary hypertension, especially in the absence of thrombus formation.

Therefore, there remains a need for additional or alternative therapies for treating, preventing and delaying pulmonary hypertension, especially potent agents with fast onset and fast offset of action.

SUMMARY OF THE INVENTION

The present invention relates to the use of a reversible $P2Y_{12}$ receptor antagonist in treating pulmonary hypertension (HP) or other related symptoms and pharmaceutical compositions or medicaments comprising a reversible $P2Y_{12}$ receptor antagonist.

A method for treating or preventing pulmonary hypertension in a subject in need thereof is provided. The method comprises administering to the subject an effective amount of a pharmaceutical composition comprising a reversible $P2Y_{12}$ receptor antagonist.

A method for reducing mortality in a subject having pulmonary hypertension is also provided. The method comprises administering to the subject an effective amount of a pharmaceutical composition comprising a reversible $P2Y_{12}$ receptor antagonist.

A method for inhibiting ADP-mediated vasoconstriction of pulmonary arteries in a subject is further provided. The method comprises administering to the subject an effective amount of a pharmaceutical composition comprising a reversible $P2Y_{12}$ receptor antagonist.

The reversible $P2Y_{12}$ receptor antagonist is preferably a rapid acting antagonist, more preferably cangrelor.

The pulmonary hypertension may be pulmonary arterial hypertension. The pulmonary arterial hypertension may be idiopathic pulmonary arterial hypertension, heritable pulmonary arterial hypertension, induced by a drug or toxin, associated with a disease, or persistent pulmonary hypertension of a newborn. The pulmonary hypertension may also be associated with pulmonary veno-occlusive disease (PVOD) or pulmonary capillary hemangiomatosis (PCH)

The pulmonary arterial hypertension inducing drug or toxin may be selected from the group consisting of aminorex, fenfluramine, dexfenfluramine, toxic rapeseed oil, cocaine, phenylpropanolamine, St. John's Wort, chemotherapeutic agents, SSRI, amphetamines, L-tryptophan and methamphetamines.

The pulmonary arterial hypertension associated disease may be a connective tissue disease, HIV infection, portal hypertension, congenital heart disease (CHD), schistosomiasis or chronic hemolytic anemia.

The pulmonary hypertension may be owing to a left heart disease. The left heart disease may be systolic dysfunction, diastolic dysfunction or valvular disease.

The pulmonary hypertension may be caused by a lung disease and/or hypoxia. The hypoxia may be caused by a lung disease, impaired control of breathing, or residence at high altitude.

Examples of the lung diseases include chronic obstructive pulmonary diseases, interstitial lung diseases, pulmonary diseases with a mixed restrictive and obstructive pattern, sleep-disordered breathing, alveolar hypoventilation disorders, chronic exposure to high altitude and developmental abnormalities. The chronic obstructive pulmonary disease may be a parenchymal lung disease. The pulmonary disease with a mixed restrictive and obstructive pattern may be chronic bronchiectasis, cystic fibrosis, or a syndrome characterized by a combination of pulmonary fibrosis and emphysema.

The pulmonary hypertension may be chronic thromboembolic pulmonary hypertension (CTEPH).

The pulmonary hypertension may be associated with a disorder selected from the group consisting of hemotologic disorders, systemic disorders, metabolic disorders, tumoral obstruction, fibrosing mediastinitis, and chronic renal failure on dialysis. The hemotologic disorder may be a myeloproliferative disorder or splenectomy. The systemic disorder may be sarcoidosis, pulmonary Langerhans cell histiocytosis, lymphangioleiomyomatosis, neurofibromatosis, or vasculitis. The metabolic disorder may be a glycogen storage disease, Gaucher disease or thyroid disorder.

In the methods according to the present invention, one or more pulmonary hypertension symptoms in the subject are preferably ameliorated. The pulmonary hypertension symptoms include shortness of breath, fatigue, dizziness, fainting, peripheral edema, bluish lips and skin, chest pain, angina pectoris, light-headedness during exercise, non-productive cough, racing pulse and palpitations. The peripheral edema may be foot, leg or ankle swelling.

The pulmonary hypertension may be postoperative pulmonary hypertension. The operation may be organ transplantation, cardiac surgery, lung resection, or thromboendarterectomy. The organ transplantation may be heart, lung, liver or kidney transplantation. The cardiac surgery may be valve repair or replacement, congenital heart repair or left-ventricular-assist device implantation. The lung resection may be pneumonectomy or lobectomy. The postoperative pulmonary hypertension may be arterial pulmonary hypertension (PAH) or pulmonary hypertension caused by a left heart disease. The postoperative pulmonary hypertension may be associated with preoperative pulmonary hypertension, fluid overload, left-ventricular failure, acute lung injury, acute respiratory distress syndrome, pulmonary emboli, acidosis, or hypoxia.

The subject is a mammal, preferably a human. The subject may be male or female. The subject may also be a newborn.

The subject may have received a pulmonary arterial hypertension inducing drug or toxin selected from the group consisting of aminorex, fenfluramine, dexfenfluramine, toxic rapeseed oil, cocaine, phenylpropanolamine, St. John's Wort, chemotherapeutic agents, SSRI, amphetamines, L-tryptophan and methamphetamines.

The subject may have suffered from a disease associated with pulmonary arterial hypertension selected from the group consisting of connective tissue diseases, HIV infection, portal hypertension, congenital heart diseases (CHD), schistosomiasis and chronic hemolytic anemia. The subject may also have suffered from pulmonary veno-occlusive disease (PVOD) or pulmonary capillary hemangiomatosis (PCH).

The subject may have suffered from a left heart disease. The left heart disease may be systolic dysfunction, diastolic dysfunction or valvular disease.

The subject may have suffered from a lung disease. The lung disease may be a chronic obstructive pulmonary disease, interstitial lung disease, pulmonary disease with a mixed restrictive and obstructive pattern, sleep-disordered breathing, alveolar hypoventilation disorder, chronic exposure to high altitude, or developmental abnormality. The chronic obstructive pulmonary disease may be a parenchymal lung disease. The pulmonary disease with a mixed restrictive and obstructive pattern may be chronic bronchiectasis, cystic fibrosis, or a syndrome characterized by a combination of pulmonary fibrosis and emphysema.

The subject may have suffered from hypoxia, impaired control of breathing, or residence at high altitude.

The subject may have suffered from a disorder selected from the group consisting of hemotologic disorders, systemic disorders, metabolic disorders, tumoral obstruction, fibrosing mediastinitis, and chronic renal failure on dialysis. The hemotologic disorder may be a myeloproliferative disorder or splenectomy. The systemic disorder may be sarcoidosis, pulmonary Langerhans cell histiocytosis, lymphangioleiomyomatosis, neurofibromatosis, or vasculitis. The metabolic disorder may be a glycogen storage disease, Gaucher disease, or thyroid disorder.

The subject may have suffered a stroke, or may not have suffered a stroke. The subject may have diabetes mellitus, or may not have diabetes mellitus. The subject may have hypertension, or may not have hypertension. The subject may have hyperlipidemia, or may not have hyperlipidemia. The subject may have suffered a myocardial infarction, or may not have suffered a myocardial infarction. The subject may have a family history of coronary artery disease (CAD), or may not have a family history of CAD. The subject may have undergone percutaneous transluminal coronary angioplasty (PTCA), or may not have undergone PTCA. The subject may have undergone percutaneous coronary intervention (PCI), or may not have undergone PCI. The subject may have undergone coronary artery bypass graft (CABG), or may not have undergone CABG. The subject may have congestive heart failure, or may not have congestive heart failure. The subject may have peripheral arterial disease (PAD), or may not have PAD. The subject may have thrombosis in an artery or vein, or may not have thrombosis in an artery or vein.

The effective amount of the pharmaceutical composition in these methods may be about 0.1-100 mg/ml cangrelor. The pharmaceutical composition may further comprise a pharmaceutically acceptable carrier or diluent.

The pharmaceutical composition may be administered to the subject in an oral dosage form, intravenous dosage form, or both. Where the pharmaceutical composition is administered to the subject in an oral dosage form, it may be administered at about 0.1-100 mg/kg cangrelor per day. Where the pharmaceutical composition is administered to the subject in a bolus intravenous dosage form, it may be administered at about 1-1000 μg/kg cagrelor. Where the pharmaceutical composition is administered to the subject in a continuous intravenous infusion dosage form, it may be administered at about 0.1-100 μg/kg/min cangrelor, and/or for a period of at least two hours.

Where the subject undergoes an operation, the pharmaceutical composition may be administered to the subject prior to the operation, preferably within two hours prior to the operation; during the operation; or after the operation, preferably within two hours, one week, or one month after the operation.

In some embodiments, the method according to the present invention further comprises administering an active agent in an effective amount for treating pulmonary hypertension. In some other embodiments, the pharmaceutical composition further comprises an active agent in an effective amount for treating pulmonary hypertension. The active agent may be selected from the group consisting of pulmonary vasodilators, digoxin, diuretics, and anticoagulants.

The pulmonary vasodilator may be selected from the group consisting of prostaglandins, endothelin receptor antagonists, phosphodiesterase type 5 inhibitors, and soluble guanylated cyclase (sGC) activators. The prostaglandin may be intravenous epoprostenol, subcutaneous or intravenous treprostinil, or inhaled iloprost. The phosphodiesterase-5 inhibitor may be sildenafil or tadalafil. The endothelin receptor antagonist may be oral bosentan or oral ambrisentan.

The method according to the present invention may further comprise performing a procedure for treating pulmonary hypertension in the subject. The procedure may be atrial septostomy, lung transplantation, or pulmonary throboendarterectomy (PTE).

The method according to the present invention may further comprise optimizing left ventricular function in the subject. The optimizing left ventricular function may comprise administering to the subject an effective amount of an active agent selected from the group consisting of diuretics, beta blockers, and ACE inhibitors. The optimizing left ventricular function may also comprise repairing or replacing a mitral valve or aortic valve in the subject.

The method according to the present invention may further comprise providing an oxygen therapy to the subject.

For each of the methods described herein, a medicament comprising an effective amount of a reversible $P2Y_{12}$ receptor antagonist is provided. The reversible $P2Y_{12}$ receptor antagonist is preferably a rapid acting antagonist, more preferably cangrelor.

The medicament is useful for treating or preventing pulmonary hypertension; reducing mortality in a subject experiencing pulmonary hypertension; or inhibiting ADP-mediated vasoconstriction of pulmonary arteries.

A medicament according to the present invention may comprise about 0.1-100 mg/ml cangrelor. It may further comprise a pharmaceutically acceptable carrier or diluent.

A medicament according to the present invention may further comprise an active agent selected from the group consisting of pulmonary vasodilators, digoxin, diuretics, anticoagulants, diuretics, beta blockers, and ACE inhibitors. The pulmonary vasodilator may be selected from the group consisting of prostaglandins, endothelin receptor antagonists, phosphodiesterase type 5 inhibitors and activators of soluble guanylated cyclase (sGC).

For each of the methods described herein, a pharmaceutical composition for treating or preventing pulmonary hypertension, reducing mortality in a subject experiencing pulmonary hypertension, or inhibiting ADP-mediated vasoconstriction of pulmonary arteries is provided. The pharmaceutical composition comprises an effective amount of a reversible $P2Y_{12}$ receptor antagonist, preferably a rapid acting antagonist, more preferably cangrelor.

A pharmaceutical composition according to the present invention may comprise about 0.1-100 mg/ml cangrelor. It may further comprise a pharmaceutically acceptable carrier or diluent.

A pharmaceutical composition according to the present invention may comprise an active agent selected from the group consisting of pulmonary vasodilators, digoxin, diuretics, anticoagulants, diuretics, beta blockers, and ACE inhibitors. The pulmonary vasodilator may be selected from the group consisting of prostaglandins, endothelin receptor antagonists, phosphodiesterase type 5 inhibitors, and activators of soluble guanylated cyclase (sGC).

A method for preparing a medicament useful for treating or preventing pulmonary hypertension, reducing mortality in a subject experiencing pulmonary hypertension, or inhibiting ADP-mediated vasoconstriction of pulmonary arteries is provided. The method comprises admixing a reversible $P2Y_{12}$ receptor antagonist with a pharmaceutically acceptable carrier or diluent. The reversible $P2Y_{12}$ receptor antagonist is preferably a rapid acting antagonist, more preferably cangrelor. The method may further comprise admixing an active agent selected from the group consisting of pulmonary vasodilators, digoxin, diuretics, anticoagulants, diuretics, beta blockers, and ACE inhibitors. The pulmonary vasodilator may be selected from the group consisting of prostaglandins, endothelin receptor antagonists, phosphodiesterase type 5 inhibitors and activators of soluble guanylated cyclase (sGC).

DETAILED DESCRIPTION OF THE INVENTION

The present invention is based on the discovery that cangrelor, a reversible and rapid acting inhibitor of the P2Y$_{12}$ receptor, is effective in attenuating ADP- and hypoxia-induced pulmonary vasoconstriction. In particular, cangrelor is effective in attenuating acute hypoxic pulmonary vasoconstriction (HPV) with fast onset of action.

Cangrelor is a nonthienopyridine adenosine triphosphate analogue, which reversibly binds to and inhibits the P2Y$_{12}$ ADP receptor. Cangrelor is direct-acting, reversible, and selective. Having a short half-life, cangrelor exhibits rapid onset and offset of effect. The chemical structure of cangrelor is shown in Formula I.

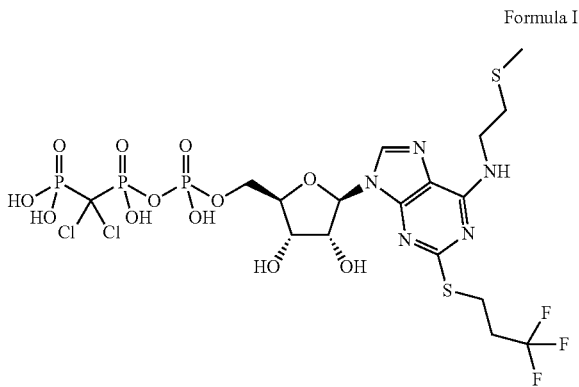 [SMILES: CSCCNc1nc(SCCC(F)(F)F)nc2c1ncn2[C@@H]1O[C@H](COP(=O)(O)OP(=O)(O)C(Cl)(Cl)P(=O)(O)O)[C@@H](O)[C@H]1O]

Formula I

The term "cangrelor" as used herein encompasses the compound of Formula I, as well as tautomeric, enantiomeric and diastereomeric forms thereof, and racemic mixtures thereof, other chemically active forms thereof, and pharmaceutically acceptable salts of these compounds, including a tetrasodium salt. These alternative forms and salts, processes for their production, and pharmaceutical compositions comprising them, are well known in the art and set forth in U.S. Pat. No. 5,721,219. Additional disclosure relevant to the production and use of cangrelor may be found in U.S. Pat. Nos. 5,955,447, 6,130,208 and 6,114,313, as well as in U.S. Appln. Publication No. 2006/0270607.

The present invention provides various methods, including a method for treating or preventing pulmonary hypertension in a subject in need thereof, a method for reducing mortality in a subject having pulmonary hypertension, and a method for inhibiting ADP-mediated vasoconstriction of pulmonary arteries in a subject. These methods comprise administering to the subject an effective amount of a pharmaceutical composition comprising a reversible P2Y$_{12}$ receptor antagonist. Examples of reversible P2Y$_{12}$ receptor antagonists include cangrelor, ticagrelor, AR-C67085, and elinogrel (PRT-060128). Preferably, the reversible P2Y$_2$ receptor antagonist is cangrelor. Other reversible P2Y$_{12}$ receptor antagonists may include compounds corresponding to formula I as set forth in U.S. Pat. No. 5,721,219, formula I as set forth in U.S. Pat. No. 5,955,447, formula I as set forth in U.S. Pat. No. 6,130,208, formula I as set forth in U.S. Pat. No. 6,114,313, or formula I as set forth in U.S. Appln. Publication No. 2006/0270607, and pharmaceutical acceptable salts thereof.

The reversible P2Y$_{12}$ receptor is preferably a rapid acting antagonist. The term "rapid acting" refers to fast onset and fast offset. A rapid acting drug reaches steady plasma drug concentration quickly (e.g., within less than about one hour, 45 minutes, 30 minutes, 15 minutes, 10 minutes, or 5 minutes after starting drug administration), and gets cleared quickly (e.g., within about five hours, three hours, one hour, 30 minutes, 15 minutes, 10 minutes, or 5 minutes after ending drug administration). Preferably, the rapid acting reversible P2Y$_{12}$ receptor is cangrelor.

The pulmonary hypertension (PH) may fall into any one of the different groups or subgroups of the PH clinical classification. For example, the PH may fall into one of the five main groups: pulmonary arterial hypertension (PAH), PH associated with left heart disease (PHLHD), PH associated with lung disease or hypoxia, chronic thromboembolic pulmonary hypertension (CTPH), and PH with unclear or multifactorial mechanisms. Criteria for diagnosis of PH are well known in the art.

The PAH is clinically defined as a group of diseases characterized by a gradual increase in pulmonary vascular resistance leading to right ventricular failure and early death. Subias et al., *Rev. Esp. Cardiol.* 63(5):583-96 (2010). A PAH diagnosis requires invasive hemodynamic criteria, including a mean pulmonary artery pressure greater than 25 mm Hg at rest and a normal pulmonary capillary wedge or left ventricular end-diastolic pressure less than 15 mm Hg. Humbert, M. *Am. J. Respir. Crit. Care Med* 179:650-6 (2009); Hill et al., *Respiratory Care* 54(7):958-68 (2009).

The PAH may be idiopathic pulmonary arterial hypertension (IPAH), heritable PAH, induced by a drug or toxin, associated with certain diseases, or persistent in a newborn. Examples of the PAH inducing drugs or toxins include aminorex, fenfluramine, dexfenfluramine, toxic rapeseed oil, cocaine, phenylpropanolamine, St. John's Wort, chemotherapeutic agents, SSRI, amphetamines, L-tryptophan and methamphetamines. The PAH associated diseases include connective tissue diseases, HIV infection, portal hypertension, congenital heart diseases (CHD), schistosomiasis, and chronic hemolytic anemia.

The PH may also be pulmonary veno-occlusive disease (PVOD) or pulmonary capillary hemangiomatosis (PCH).

In the PH associated with left heart disease (PHLHD), the left heart disease may be systolic dysfunction, diastolic dysfunction, or valvular disease.

The PH may be caused by a lung disease and/or hypoxia. Hypoxia is a pathological condition in which oxygen does not reach body tissues due to inadequate oxygen supply, and may be caused by a lung disease, impaired control of breathing, or residence at high altitude. A lung disease may be selected from the group consisting of chronic obstructive pulmonary diseases, interstitial lung diseases, pulmonary diseases with a mixed restrictive and obstructive pattern, sleep-disordered breathing, alveolar hypoventilation disorders, chronic exposure to high altitude and developmental abnormalities. The chronic obstructive pulmonary disease may be a parenchymal lung disease. The pulmonary disease with a mixed restrictive and obstructive pattern may be chronic bronchiectasis, cystic fibrosis, or a syndrome characterized by a combination of pulmonary fibrosis and emphysema.

Chronic thromboembolic pulmonary hypertension (CTEPH) is a frequent cause of PH, especially among patients after an acute pulmonary embolism. Currently, the only curative treatment of CTEPH is pulmonary thromboendarterectomy.

The PH may also be associated with other various disorders, for example, hemotologic disorders (e.g., myeloproliferative disorders and splenectomy), systemic disorders (e.g.,sarcoidosis, pulmonary Langerhans cell histiocytosis, lymphangioleiomyomatosis, neurofibromatosis, and vasculitis), metabolic disorders (e.g., glycogen storage disease, Gaucher disease, and thyroid disorder), tumoral obstruction, fibrosing mediastinitis, and chronic renal failure on dialysis.

In some embodiments, the PH is postoperative PH. Postoperative PH could fall into any of the groups or subgroups of PH as set forth in the updated PH clinical classification. Preferably, the postoperative PH is PAH (e.g., congenital heart disease or portopulmonary hypertension preliver transplant) or PHLHD (e.g., chronic heart failure pre-transplant or left-ventricular diastolic dysfunction). The postoperative PH may be caused by organ transplantation, cardiac surgery, lung resection or thromboendarterectomy. The organ transplantation may be heart, lung, liver or kidney transplantation. The cardiac surgery may be valve repair or replacement, congenital heart repair, or left-ventricular-assist device implantation. The lung resection may be pneumonectomy or lobectomy. The postoperative HP may also be caused by factors indirectly associated with a surgery or procedure. Such factors include preoperative pulmonary hypertension, fluid overload, left-ventricular failure, acute lung injury or acute respiratory distress syndrome, pulmonary emboli, and acidosis and hypoxia.

The subject may be a mammal, for example, a mouse, rat, dog, pig, or human, preferably a human. The subject may be male or female. The subject may also be a newborn. Preferably, the subject is at risk or has suffered from PH or ADP-mediated vasoconstriction of pulmonary arteries. More preferably, the subject exhibits one or more PH symptoms.

In a method in accordance with the present invention, a pulmonary hypertension symptom in the subject is preferably ameliorated or improved. Examples of the PH symptoms include shortness of breath, fatigue, dizziness, fainting, peripheral edema (swelling in foot, legs or ankles, bluish lips and skin, chest pain, angina pectoris, light-headedness during exercise, non-productive cough, racing pulse and palpitations.

The subject may have received a PAH inducing drug or toxin. PAH inducing drugs or toxins include aminorex, fenfluramine, dexfenfluramine, toxic rapeseed oil, cocaine, phenylpropanolamine, St. John's Wort, chemotherapeutic agents, SSRI, amphetamines, L-tryptophan and methamphetamines.

The subject may have suffered from a PAH associated disease selected from the group consisting of connective tissue diseases, HIV infection, portal hypertension, congenital heart diseases (CHD), schistosomiasis and chronic hemolytic anemia.

The subject may have suffered from a pulmonary veno-occlusive disease (PVOD) or pulmonary capillary hemangiomatosis (PCH).

The subject may have suffered from a left heart disease. The left heart disease may be systolic dysfunction, diastolic dysfunction or valvular disease.

The subject may have suffered from a lung disease, hypoxia, impaired control of breathing or residence at high altitude. Examples of lung diseases include chronic obstructive pulmonary diseases, interstitial lung diseases, pulmonary diseases with a mixed restrictive and obstructive pattern, sleep-disordered breathing, alveolar hypoventilation disorders, chronic exposure to high altitude and developmental abnormalities. The chronic obstructive pulmonary disease may be a parenchymal lung disease. The pulmonary disease with a mixed restrictive and obstructive pattern may be chronic bronchiectasis, cystic fibrosis, or a syndrome characterized by a combination of pulmonary fibrosis and emphysema.

The subject may have suffered from one or more other PH associated disorders, including hemotologic disorders, systemic disorders, metabolic disorders, tumoral obstruction, fibrosing mediastinitis, and chronic renal failure on dialysis. The hemotologic disorder may be a myeloproliferative disorder or splenectomy. The systemic disorder may be sarcoidosis, pulmonary Langerhans cell histiocytosis, lymphangioleiomyomatosis, neurofibromatosis or vasculitis. The metabolic disorder may be a glycogen storage disease, Gaucher disease or thyroid disorder.

The subject may have suffered a stroke, or the subject may not have suffered a stroke. The subject may have diabetes mellitus, or the subject may not have diabetes mellitus. The subject may have hypertension, or the subject may not have hypertension. The subject may have hyperlipidemia, or the subject may not have hyperlipidemia. The subject may have suffered a myocardial infarction, or the subject may not have suffered a myocardial infarction. The subject may have a family history of coronary artery disease (CAD), or the subject may not have a family history of CAD. The subject may have undergone percutaneous transluminal coronary angioplasty (PTCA), or the subject may not have undergone PTCA. The subject may have undergone percutaneous coronary intervention (PCI), or the subject may not have undergone PCI. The subject may have undergone coronary artery bypass graft (CABG), or the subject may not have undergone CABG. The subject may have congestive heart failure, or the subject may not have congestive heart failure. The subject may have peripheral arterial disease (PAD), or the subject may not have PAD. The subject may have thrombosis in an artery or vein, or the subject may not have thrombosis in an artery or vein.

The term "an effective amount" refers to an amount of a pharmaceutical composition comprising a reversible $P2Y_{12}$ receptor antagonist (e.g., cangrelor) required to achieve a stated goal (e.g., treating or preventing PH, reducing mortality, and/or inhibiting ADP-mediated vasoconstriction of pulmonary arteries). The effective amounts of the pharmaceutical compositions comprising a reversible $P2Y_{12}$ receptor antagonist (e.g., cangrelor) may vary depending upon the stated goals, the physical characteristics of the subject, the nature and severity of the PH, existence of related or unrelated medical conditions, the nature of the reversible $P2Y_{12}$ receptor antagonist, the composition comprising the reversible $P2Y_{12}$ receptor antagonist (e.g., cangrelor), the means of administering the drug to the subject, and the administration route. A specific dose for a given subject may generally be set by the judgment of a physician. The pharmaceutical composition may be administered to the subject in one or multiple doses.

The pharmaceutical composition may comprise about 0.1-100, 0.1-50, 0.1-25, 0.1-20, 0.1-10, 0.1-5, 0.1-2.5, 0.1-2, 0.1-1, 0.1-0.5, or 0.1-0.2 mg/ml (e.g., about 0.5, 1, 2, 3, 4, 5, 6, 7, 8, 9 and 10 mg/ml). The pharmaceutical composition may further comprise a pharmaceutically acceptable carrier or diluent. Suitable carriers, diluents and excipients are well known in the art.

The pharmaceutical composition may be administered to the subject for a period of hours, days, weeks or months. It may also be administered once, twice, thrice or more times a day, once every two days, once every three days, once every four days, once every five days, once every six days, once a week, once every 10 days, once every two weeks, once every three weeks, once a month, or even less frequently.

The pharmaceutical compositions of the present invention may be formulated, for example, for oral, sublingual, intranasal, intraocular, rectal, transdermal, mucosal, topical or parenteral administration. Parenteral administration may be intradermal, subcutaneous (s.c., s.q., sub-Q, Hypo), intramuscular (i.m.), intravenous (i.v.), intraperitoneal (i.p.), intra-arterial, intramedulary, intracardiac, intra-articular (joint), intrasynovial (joint fluid area), intracranial, intraspinal, and intrathecal (spinal fluids). Any device suitable for parenteral injection or infusion of drug formulations may be used for such administration. According to the present invention, the pharmaceutical compositions are preferably administered to the subject in an oral dosage form, an intravenous dosage form, or both. The intravenous dosage form may be a bolus intravenous dosage form or a continuous intravenous infusion dosage form.

When administered as an intravenous (IV) formulation, the pharmaceutical composition may be administered as a bolus or as a continuous infusion. When administered in a bolus dosage form, the pharmaceutical compositions may be administered to the subject at about 1-1000, 1-500, 1-200, 1-100, 1-75, 1-50, 1-40, 1-30, 1-20, or 1-10 µg cangrelor per kg body weight (e.g., about 1, 5, 10, 15, 20, 25, 30, 35, 40, 45, 50, 55, 60, 65, 70, 75, 80, 85, 90, 95 or 100 µg/kg), preferably about 20-40 µg/kg, more preferably about 30 µg/kg. When administered as a continuous intravenous infusion dosage form, the pharmaceutical composition may be administered to the subject at about 0.1-100, 0.1-50, 0.1-25, 0.1-10, 0.1-7.5, 0.1-5, 0.1-2.5, 0.1-2, 0.1-1, or 0.1-0.5 µg cangrelor per kg body weight per minute (e.g., about 0.1, 0.5, 1, 2, 5, 7.5, 10, 15, 20, 25, or 30 µg/kg/min), preferably about 1-10 µg/kg/min, more preferably about 4 ug/kg/min. The pharmaceutical composition may be administered continuously for a period of at least about 0.1, 0.2, 0.5, 1, 1.5, 2, 2.5, 3, 3.5, or 4 hours.

When administered orally, the pharmaceutical composition may be administered to the subject in an oral dosage at about 0.1-1000, 0.1-500, 0.1-250, 0.1-100, 0.1-50, 1-50, 1-40, 1-30, 1-20, 1-10, or 1-5 mg cangrelor per kg body weight per day (e.g., about 1, 2, 3, 4, 5, 10, 15, 20, 25, 30, 40, 50, 100 or 500 mg/kg/day), preferably about 5-30 mg/kg/day, more preferably about 5, 10, 15, 20, 25, or 30 mg/kg/day. Oral administration may be as a single dose (bolus) or divided into multiple doses. When multiple doses are administered orally, administration may be once, twice, thrice or more times per day.

In the method for treating or preventing pulmonary hypertension (PH) or reducing mortality in a subject having pulmonary hypertension (PH), administering an effective amount of the pharmaceutical composition comprising cangrelor may follow PH diagnosis or onset of one or more of the PH symptoms. In the method for inhibiting ADP-mediated vasoconstriction of pulmonary arteries in a subject, the administration may start after ADP-mediated vasoconstriction of pulmonary arteries is observed or suspected in the subject. Preferably, the pharmaceutical composition is administered to the subject within about 5, 10, 30, 60, 90 or 120 minutes of the PH diagnosis or the onset of one or more PH symptoms. The course of treatment may last for a period of hours, days, weeks or months. In preferred embodiments, the mortality is reduced by at least about 0.05%, 0.1%, 0.2%, 0.4%, 0.6%, 0.8%, 1.0%, 1.2%, 1.5%, 2%, or 5%.

Where the subject undergoes an operation, the pharmaceutical composition may be administered to the subject prior to the operation (e.g., within 0.5, 1, 1.5, 2, 2.5, 3, 3.5, or 4 hours before starting the operation), during the operation, or after the operation (e.g., within 0.5, 1, 1.5, 2, 2.5, 3, 3.5, or 4 hours, 1 week, or 1 month after ending the operation). An operation may be a surgery (e.g., heart, lung, liver and kidney transplantation) or a procedure (e.g., valve repair/replacement, congenital heart repair, and left-ventricular-assist device implantation). A skilled artisan will understand that different dosages may be administered at different time points. Thus, the dosages may differ in the periods before, during, and after the operation.

The methods according to the present invention may further comprise administering an active agent in an effective amount for treating PH or optimizing left ventricular function in the subject. Suitable active agents may be administered to the subject in the same composition comprising cangrelor or in a separation composition simultaneously or sequentially.

Suitable active agents for treating PH include pulmonary vasodilators, digoxin, diuretics, and anticoagulants. Examples of the pulmonary vasodilator include prostaglandins, endothelin receptor antagonists, phosphodiesterase type 5 inhibitors, and soluble guanylated cyclase (sGC) activators. The prostaglandin may be intravenous epoprostenol, subcutaneous or intravenous treprostinil, or inhaled iloprost. The phosphodiesterase-5 inhibitor may be sildenafil or tadalafil. The endothelin receptor antagonist may be oral bosentan or oral ambrisentan.

Suitable active agents for optimizing left ventricular function include diuretics, beta blockers, and ACE inhibitors.

The methods according to the present invention may also include a procedure for treating PH (e.g., atrial septostomy, lung transplantation, and pulmonary throboendarterectomy (PTE)), or for optimizing left ventricular function (e.g., repair or replacement of a mitral valve or aortic valve).

The methods according to the present invention may further comprise providing an oxygen therapy to the subject.

Each of the methods according to the present invention may include an additional step of measuring the effect or effectiveness of the pharmaceutical composition during or after administration. For example, the additional step of measuring an effect of the pharmaceutical composition may be performed about 1, 2, 5, 10, 15, 30, or 45 min, or 1, 5, 10, 15, 20 or 24 hours, or more, after the completion of the method. The measuring step may include determining one or more haemodynamic measurements, including mean pulmonary artery pressure (MPAP), pulmonary vascular resistance (PVR), pulmonary capillary wedge pressure (PCWP), cardiac output (CO), systemic vascular resistance (SVR), mean right atrial pressure (MRAP), mean aortic blood pressure (MAP), heart rate (HR), stroke volume (SV) and blood-O2-consumption. Methods for determining these measurements are well known in the art.

In some embodiments, medicaments comprising an effective amount of a reversible $P2Y_{12}$ receptor antagonist is provided. They are useful for treating or preventing pulmonary hypertension, reducing mortality in a subject experiencing pulmonary hypertension, or inhibiting ADP-mediated vasoconstriction of pulmonary arteries. The reversible $P2Y_{12}$ receptor antagonist is preferably a rapid acting antagonist, more preferably cangrelor.

The medicaments may comprise cangrelor in an amount of about 0.1-100, 0.1-50, 0.1-25, 0.1-20, 0.1-10, 0.1-5, 0.1-2.5, 0.1-2, 0.1-1, 0.1-0.5, or 0.1-0.2 mg/ml, preferably about 0.5, 1, 2, 3, 4, 5, 6, 7, 8, 9 or 10 mg/ml. The medicaments may further comprise a pharmaceutically acceptable carrier or diluent, and/or an active agent suitable for treating PH or for optimizing left ventricular function.

In some other embodiments, methods for preparing the medicaments according to the present invention are provided. The preparation methods comprise admixing a reversible $P2Y_{12}$ receptor antagonist, preferably a rapid acting antagonist, more preferably cangrelor, with a pharmaceutically acceptable carrier or diluent. The methods may further comprise admixing an active agent suitable for treating PH or for optimizing left ventricular function. The method may further comprise admixing an active agent selected from the group consisting of pulmonary vasodilators, digoxin, diuretics, anticoagulants, diuretics, beta blockers, and ACE inhibitors. The pulmonary vasodilator may be selected from the group consisting of prostaglandins, endothelin receptor antagonists, phosphodiesterase type 5 inhibitors and activators of soluble guanylated cyclase (sGC).

The term "about" as used herein when referring to a measurable value such as an amount, a percentage, and the like, is meant to encompass variations of ±20% or ±10%, more preferably ±5%, even more preferably ±1%, and still more preferably ±0.1% from the specified value, as such variations are appropriate.

EXAMPLE 1

P2Y$_{12}$ Receptor Antagonism with Cangrelor Attenuates ADP- and Hypoxia-Induced Pulmonary Vasoconstriction Hypoxic pulmonary vasoconstriction (HPV) may lead to pulmonary hypertension, right heart failure and death. As nucleotides may be released in hypoxia to influence vascular tone and ADP increases pulmonary artery pressure, the ADP P2Y$_{12}$ receptor antagonist cangrelor was studied for its effects on pulmonary vasoconstriction induced by ADP and hypoxia.

Haemodynamic measurements were performed in six anaesthetized, mechanically ventilated pigs (30.2±0.7 kg) in normoxia ($F_iO_2$~0.21) and hypoxia ($F_iO_2$~0.10) prior to and during right atrial cangrelor infusion at a loading dose of 30 µg/kg/min for 10 min, and then a continuous infusion at 4 µg/kg/min for 80 min. Another six pigs (29.3±0.5 kg) were investigated in normoxia before and during right atrial infusion of ADP at 70 µg/kg/min for ~7 min; as well as before and during simultaneous ADP and cangrelor infusion for ~7 min at doses of 70 µg/kg/min and 4 µg/kg/min, respectively, after a cangrelor loading dose of 30 µg/kg/min for 10 min. All data are mean±SEM.

Protocol 1—Response to hypoxia. Compared to normoxia ($F_iO_2$~0.21), hypoxia ($F_iO_2$~0.10); increased mean pulmonary artery pressure (MPAP) by 10.9±1.2 mmHg (p<0.05), pulmonary vascular resistance (PVR) by 1.6±0.3 WU (p<0.001), pulmonary capillary wedge pressure (PCWP) by 1.3±0.6 mmHg (p<0.038) and cardiac output (CO) by 0.9±0.3 1·min$^{-1}$ (p<0.009); and decreased systemic vascular resistance (SVR) by 4.9±1.7 WU (p<0.015); whereas mean right atrial pressure (MRAP), mean aortic blood pressure (MAP), heart rate (HR), stroke volume (SV) and blood-O$_2$-consumption were unaltered (p=ns).

Protocol 2—Response to cangrelor during hypoxia. Compared to hypoxia baseline, MPAP decreased transiently by 3.3±0.4 (p<0.036) and 3.6±0.6 mmHg (p<0.018), respectively, 10 and 30 min after initiation of cangrelor infusion; but returned to levels not different (p=ns) from baseline 60 and 90 min after initiation of cangrelor infusion. PVR, MRAP, PCWP, MAP, SVR, CO, HR, SV and blood-O$_2$-consumption were unaltered by cangrelor infusion during hypoxia (p=ns).

Protocol 3—Response to ADP during normoxia. ADP infusion during normoxia increased MPAP, temporarily to peak at 35.2±1.9 mmHg, 19.3±1.6 mmHg higher (p<0.001) than baseline, to then stabilize at a level 10.4±1.6 mmHg higher (p<0.001) than baseline, and 8.9±1.4 mmHg lower (p<0.001) than the peak, after ~4-7 min. Also, after ~4-7 min from initiation of ADP infusion, PVR had increased (p<0.002) by 2.8±0.4 WU and PCWP by 2.5±0.7 mmHg (p<0.019), compared to baseline. ADP infusion during normoxia decreased MAP, first to reach a nadir at 39.8±6.1 mmHg, 48.5±6.0 mmHg lower (p<0.001) than baseline, however, then stabilizing, after ~4-7 min, at a level not different (p=ns) from, although slightly lower than, baseline, and 41.7±8.9 mmHg higher (p<0.001) than the nadir. MRAP, SVR, CO, HR, SV and blood-O$_2$-consumption were unchanged (p=ns) by ADP infusion during normoxia. However, MRAP tended to increase (p=ns); whereas CO, SV and blood-O$_2$-consumption tended to decrease (p=ns) with ADP infusion.

Protocol 4—Response to simultaneous ADP and cangrelor infusion. With simultaneous ADP and cangrelor infusion during normoxia, after the loading dose of cangrelor, MPAP first, transiently increased by 7.3±1.8 mmHg (p<0.05), compared to baseline, to reach a peak that was ~66% of the peak ADP response without cangrelor (p<0.001), and then returned to a level not different (p=ns) from baseline, however, 7.4±1.5 mmHg lower (p<0.05) than the peak, after ~4-7 min. The ~4-7 min MPAP measurement was, hence, significantly lower (p<0.002) with simultaneous ADP and cangrelor infusion, as compared to with ADP infusion alone. During the same conditions, MAP first, transiently decreased (p<0.001) by 19.4±3.1 mmHg, compared to baseline, to reach a nadir at 64.9±3.4 mmHg, significantly higher (p<0.027) than the nadir response to ADP alone, and then, stabilized at a level 6.5±1.2 mmHg lower (p<0.01) than baseline, and 12.9±2.2 mmHg higher (p<0.001) than the nadir, after ~4-7 min. The ~4-7 min MAP measurement after simultaneous ADP and cangrelor infusion was, however, not different (p=ns) from the measurement with ADP infusion alone. Also, SVR decreased (p<0.024) by 3.2±1.2 WU, as compared to baseline, in response to simultaneous ADP and cangrelor infusion. However, the ~4-7 min SVR measurement after simultaneous ADP and cangrelor infusion did not differ (p=ns) from the measurement with ADP infusion alone. During the same conditions; PVR, MRAP, PCWP, CO, HR, SV and blood-O$_2$-consumption were unchanged (p=ns), although blood-O$_2$-consumption tended to decrease (p=ns). Furthermore, the ~4-7 min PVR and PCWP measurements after simultaneous ADP and cangrelor infusion were lower (p<0.005 and p<0.022, respectively) than the measurements with ADP infusion alone. Also, the ~4-7 min SV measurement after simultaneous ADP and cangrelor infusion was higher (p<0.02) than the measurement with ADP infusion alone. Cangrelor infusion alone during normoxia did not alter (p=ns) any of the variables. There were neither any differences (p=ns) in between the baseline measurements of any parameters in protocol 3 and 4 or the ~4-7 min measurements of MRAP, CO, HR and blood-O$_2$-consumption with ADP infusion alone and simultaneous ADP and cangrelor infusion.

Cangrelor temporarily attenuated acute HPV with a ~12 and ~14% MPAP decrease 10 and 30 min after cangrelor infusion was initiated, respectively, without affecting MAP, SVR and blood-O$_2$-consumption. Cangrelor furthermore attenuated 34% of the MPAP peak and totally prevented the sustained MPAP and PVR increases induced by ADP infusion during normoxia. These data show that ADP is involved in modulating HPV and that ADP-induced pulmonary vasoconstriction is at least partially mediated by the P2Y$_{12}$ receptor. P2Y$_{12}$ receptor antagonism with cangrelor thus is potentially useful in attenuating hypoxia-induced pulmonary hypertension. Furthermore, the MAP decrease to ADP was attenuated with cangrelor, as was the PCWP increase and the trend for a SV decrease with ADP infusion alone.

All documents, books, manuals, papers, patents, published patent applications, guides, abstracts, and other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed:

1. A method of treating pulmonary hypertension in a subject in need thereof, consisting essentially of administering to the subject a pharmaceutical composition consisting essentially of (a) an active ingredient, wherein the active ingredient is cangrelor; and (b) optionally one or more pharmaceutically acceptable carriers, a second agent as diluents, a third agent as excipients, or a combination thereof; and performing a measurement to determine the decrease of mean pulmonary artery pressure after administration of cangrelor.

2. A method of reducing mortality in a subject experiencing pulmonary hypertension, consisting essentially of administering to the subject a composition consisting essentially of (a) an active ingredient, wherein the active ingredient cangrelor; and (b) optionally one or more pharmaceutically acceptable carriers, a second agent as diluents, a third agent as excipients, or a combination thereof; and performing a measurement to determine the decrease of mean pulmonary artery pressure after administration of cangrelor.

3. A method of inhibiting ADP-mediated vasoconstriction of pulmonary arteries in a subject in need thereof, consisting essentially of administering to the subject a composition consisting essentially of (a) an active ingredient, wherein the active ingredient is-cangrelor; and (b) optionally one or more pharmaceutically acceptable carriers, a second agent as diluents, a third agent as excipients, or a combination thereof; and performing a measurement to determine the decrease of mean pulmonary artery pressure after administration of cangrelor.

4. The method of claim 1, wherein the administration of cangrelor comprises a dose of about 0.1-100 mg/ml.

5. The method of claim 1, wherein the administration of cangrelor comprises intravenous administration.

6. The method of claim 5, wherein the administration of cangrelor comprises a bolus, a continuous infusion, or a combination thereof.

7. The method of claim 6, wherein the administration of cangrelor comprises a bolus followed by a continuous infusion.

8. The method of claim 6, wherein the administration of cangrelor comprises a bolus of about 1-100 µg/kg body weight.

9. The method of claim 6, wherein the administration of cangrelor comprises continuous infusion of about 0.1 to 25 µg/kg body weight /min.

10. The method of claim 6, wherein the administration of cangrelor comprises continuous infusion for a period of at least about 4 hours.

11. The method of claim 1, wherein the pharmaceutical composition consists essentially of cangrelor and one or more pharmaceutically acceptable carriers, a second agent as diluents, or a combination thereof.

12. The method of claim 1, wherein the subject has suffered a stroke or a myocardial infarction.

13. The method of claim 1, wherein the subject has diabetes mellitus, hyperlipidemia, congestive heart failure, peripheral arterial disease (PAD), thrombosis in an artery or vein, or a family history of coronary artery disease (CAD).

14. The method of claim 1, wherein the subject has undergone percutaneous transluminal coronary angioplasty (PTCA), coronary intervention (PCI), or artery bypass graft (CABG).

15. The method of claim 1, wherein the subject has pulmonary arterial hypertension.

* * * * *